US008445256B2

(12) United States Patent
Woods et al.

(10) Patent No.: US 8,445,256 B2
(45) Date of Patent: May 21, 2013

(54) LIQUID MYCORRHIZA COMPOSITIONS

(75) Inventors: Kristi Woods, Blacksburg, VA (US); Erin Divers, Forest, VA (US)

(73) Assignee: Novozymes A/S, Bagsvaerd (DK)

( * ) Notice: Subject to any disclaimer, the term of this patent is extended or adjusted under 35 U.S.C. 154(b) by 918 days.

(21) Appl. No.: 12/178,864

(22) Filed: Jul. 24, 2008

(65) Prior Publication Data

US 2009/0035843 A1 Feb. 5, 2009

Related U.S. Application Data

(60) Provisional application No. 60/951,503, filed on Jul. 24, 2007.

(51) Int. Cl.
*A01N 65/00* (2009.01)
*A01N 63/00* (2006.01)
*C12N 9/00* (2006.01)
*C12N 1/00* (2006.01)

(52) U.S. Cl.
USPC ........ 435/256.8; 424/93.5; 435/183; 504/117

(58) Field of Classification Search
None
See application file for complete search history.

(56) References Cited

U.S. PATENT DOCUMENTS

2004/0208852 A1   10/2004   Coughlan et al.

FOREIGN PATENT DOCUMENTS

| CN | 1420167 | | 5/2003 |
|---|---|---|---|
| EP | 1 840 110 | | 10/2007 |
| JP | 4141023 | | 5/1992 |
| WO | WO9508521 | * | 3/1995 |
| WO | WO 2006/060968 | | 6/2006 |

OTHER PUBLICATIONS

Cairney et al. Naturwissenschaften. Nov. 2000;87(11):467-75.*
Brundrett et al. Biol Rev Camb Philos Soc. Aug. 2004;79(3):473-95.*
Backman et al., "Effect of Carbofuran and Other Pesticides on Vesicular Arbuscular Mycorrhizae In Peanuts", Nematropica, Organization of Tropical American Nematologists, vol. 7, No. 1, pp. 13-17 (1977) Xp008106637.
Vijayakumar et al., "Suppression Of Pathogenic Activity by Dual Inoculation and the Effect Of Some Biocides On Am Inoculated Endemic Trees Of Western Ghats", Ecology, Environment And Conservation, Enviromedia, vol. 9, No. 4, pp. 469-475 (2003).
Colinas, et al., "Ectomycorrhizas and Rhizosphere Microorganisms of Seedlings of *Pseudotsuga menziesii* (Mirb.) Franco Planted on a Degraded Site and Inoculated with Forest Soils Pretreated with Selective Biocides" New Phytologist, vol. 127, No. 3, pp. 529-537 (1994).
Database Wpi Week 199227 Thomson Scientific, London, Gb; An 1992-221435 Xp002535734 May 14, 1992 Abstract.
Spokes, et al., "Effects Of Plant Protection Chemicals On Vesicular-Arbuscular Mycorrhizas", Chemical Abstracts Service, Columbus Xp002529630 (1981).
Kelley, Walter et al., "Effects Of Sodium Azide And Methyl Bromide On Soil Bacterial Populations, Enzymic Activities And Other Biological Variables" Pesticide Science, vol. 10, No. 3, pp. 207-215 (1979).
Spokes, et al., "Effects Of Sodium Azide And Methyl Bromide On Soil Bacterial Populations, Enzymic Activities and Other Biological Variables" Pesticide Science, vol. 12, No. 3, pp. 346-350 (1981).
Saleh Al-Gami, World Journal of Agricultural Sciences, vol. 2, No. 3, pp. 303-310 (2006).
Schreiner et al., Biol. Fertil. Soils, vol. 24, pp. 18-26 (1997).
West et al., Journal of Ecology, vol. 81, pp. 345-350 (1993).

* cited by examiner

*Primary Examiner* — Christian Fronda
(74) *Attorney, Agent, or Firm* — Thomas C. Sova, IV

(57) ABSTRACT

The present invention relates to liquid mycorrhiza compositions and to methods for colonizing a plant, grass, tree or shrub with one or more mycorrhizas.

21 Claims, No Drawings

LIQUID MYCORRHIZA COMPOSITIONS

CROSS-REFERENCE TO RELATED APPLICATIONS

This application claims priority or the benefit under 35 U.S.C. 119 of U.S. provisional application No. 60/951,503 filed Jul. 24, 2007, the contents of which are fully incorporated herein by reference.

BACKGROUND OF THE INVENTION

1. Field of the Invention

The present invention relates to liquid mycorrhiza compositions and to methods for colonizing a plant, grass, tree or shrub with one or more mycorrhizas. Specifically, it relates to compositions which improve the ability of the mycorrhizas to colonize plant roots, resulting in greater efficacy of plant treatment formulations which contain the mycorrhizas.

2. Description of Related Art

Mycorrhizas are symbiotic associations between fungi and the roots of plants. In a mycorrhizal association, the fungus may colonize the roots of a host plant either intercellularly, intracellularly or extracellularly. The functional symbiosis provides a suitable and sufficient carbohydrate source for the fungal symbiont. The plant symbiont benefits can be numerous and include improved nutrient and water uptake, additional carbon acquisition, increased sink strength for photosynthate translocation, increased production of phytohormones, improved resistance to pathogens, and heavy metal tolerance. Mycorrhizas are critically important organs for resource uptake by most terrestrial plants. In the absence of an appropriate fungal symbiont, many terrestrial plants suffer from resource limitations and ultimately reduced growth, and fitness.

Mycorrhizas are added to fertilizer products to incorporate beneficial mycorrhizas in the fertilizer blends. Current fertilizer blends contain mycorrhizas in the form of a dry granular product or a wettable powder product. Mycorrhizas have not been added to liquid fertilizers due to stability issues.

Production of mycorrhizas is challenging because they have unique growth requirements. Endomycorrhizas (also called vesicular arbuscular mycorrhizas, VAM, or arbuscular mycorrhizas, AM) are obligate symbionts with plants. The predominant method used to cultivate the endomycorrhizas is with a host plant under controlled conditions.

Bactericides are commonly used to eliminate unwanted bacterial contamination. The preservatives used at low rates are designed to kill vegetative bacteria while leaving spores unharmed. Kathon (methylchloroisothiazolinone and methylisothiazolinone) and Bronopol (2-bromo-2-nitro-1,3-propanediol) are two bactericides used as preservatives. Kathon has a broad antimicrobial spectrum. It is effective against gram-negative and gram-positive bacteria, fungi, and yeasts. Bronopol is effective in killing gram-negative and gram-positive bacteria. Depending on the amount used, the bactericide can kill bacteria or keep them in the spore form.

CN 1420167 discloses liquid inoculants basically connected with ectomycorrhizas.

JP 4141023 discloses a liquid medium comprising a stabilizer (citric acid or its salt form) to protect the spores.

US 2004/0208852 discloses a method of colonizing a plant with mycorrhiza.

WO 2006/060968 discloses a liquid mycorrhizal inoculant.

Schreiner et al. (*Biol. Fertil. Soils*, 1997, 24:18-26) describe the effects of biocides on arbuscular mycorrhizas.

Al-Garni (*World Journal of Agricultural Sciences*, 2006, 2(3): 303-310) describes the influence of malathion and mancozeb on mycorrhizal colonization.

West et al. (*Journal of Ecology*, 1993, 81(2): 345-350) describe the influence of three biocides on the fungal associates of the roots of *Vulpia ciliata*.

It is an object of the present invention to provide a liquid mycorrhiza composition comprising mycorrhiza which increases mycorrhizal colonization.

SUMMARY OF THE INVENTION

The present invention relates to liquid mycorrhiza compositions and to methods for increasing mycorrhizal colonization of a plant.

DETAILED DESCRIPTION OF THE INVENTION

The present invention relates to liquid compositions comprising one or more mycorrhizas and a bactericide and/or bacteriostat, and to methods for increasing mycorrhizal colonization of a plant. Improved colonization of roots by mycorrhizas leads to better plant growth and yield.

The mycorrhiza is present in the liquid compositions in an amount of 0.2-5%, preferably 0.33-3.3% weight/volume.

The bactericide and/or bacteriostat is present in an amount of 50-3,000 ppm of the active ingredient, preferably 150-2,000 ppm.

Mycorrhizas

The mycorrhizas contained in the liquid compositions of the present invention can be any mycorrhiza. The two most common types of mycorrhizas are ectomycorrhizas and endomycorrhizas (more commonly known as arbuscular mycorrhizas).

Endomycorrhizas

Arbuscular mycorrhizas, or AM (formerly known as vesicular-arbuscular mycorrhizas), are an example of a mycorrhiza that involves entry of the hyphae into the plant root cell walls to produce structures that are either balloon-like (vesicles) or dichotomously-branching invaginations (arbuscules). The fungal hyphae do not in fact penetrate the protoplast (i.e., the interior of the cell), but invaginate the cell membrane. The structure of the arbuscules greatly increases the contact surface area between the hypha and the cell cytoplasm to facilitate the transfer of nutrients between them.

Arbuscular mycorrhizas are formed only by fungi in the division Glomeromycota, which are typically associated with the roots of herbaceous plants, but may also be associated with woody plants. Fossil evidence and DNA sequence analysis suggest that this mutualism appeared 400-460 million years ago, when the first plants were colonizing land. Arbuscular mycorrhizas were likely to have been very helpful at that time, protecting plants from adverse conditions such as lack of water and nutrients.

Arbuscular mycorrhizal fungi are quite extraordinary organisms. First they have been asexual for many million years and secondly, individuals can contain many genetically different nuclei (a phenomenon called heterokaryosis).

This type of association is found in 85% of all plant families in the wild, including many crop species such as grains.

Preferably, the endomycorrhiza is of the phylum Glomeromycota and genera *Glomus* and *Gigaspora*. In a preferred embodiment, the endomycorrhiza is a strain of *Glomus*, such as *Glomus aggregatum*, *Glomus brasilianum*, *Glomus clarum*, *Glomus deserticola*, *Glomus etunicatum*, *Glomus fasciculatum*, *Glomus intraradices*, *Glomus monosporum*, or *Glomus mosseae*, or a strain of *Gigaspora margarita*.

Ectomycorrhizas

Ectomycorrhizas, or EcM, typically form between the roots of woody plants and fungi belonging to the divisions Basidiomycota, Ascomycota, or Zygomycota.

These are external mycorrhizas that form a cover on root surfaces and between the root's cortical cells.

Besides the mantle formed by the mycorrhizas, most of the biomass of the fungus is found branching into the soil, with some extending to the apoplast, stopping short of the endodermis.

Found in 10% of plant families, mostly woody species, including the oak, pine, eucalyptus, dipterocarp, and olive families.

Preferably, the ectomycorrhiza is of the phylum Basidiomycota. In a preferred embodiment, the ectomycorrhiza is a strain of *Laccaria bicolor, Laccaria laccata, Pisolithus tinctorius, Rhizopogon amylopogon, Rhizopogon fulvigleba, Rhizopogon luteolus, Rhizopogon villosuli, Sclerodenna cepa,* or *Scleroderma citrinum.*

Other Forms of Mycorrhizas

Arbuscular and ectomycorrhizas form ericoid mycorrhiza with many plants belonging to the order Ericales, while some Ericales form arbutoid and monotropoid mycorrhizas. All orchids are mycoheterotrophic at some stage during their lifecycle and form orchid mycorrhizas with a range of basidiomycete fungi.

The mycorrhiza may be an ericoid mycorrhiza, preferably of the phylum Ascomycota, such as *Hymenoscyphous ericae* or *Oidiodendron* sp.

The mycorrhiza also may be an arbutoid mycorrhiza, preferably of the phylum Basidiomycota.

In addition, the mycorrhiza may be a monotripoid mycorrhiza, preferably of the phylum Basidiomycota.

The mycorrhiza also may also be an orchid mycorrhiza, preferably of the genus *Rhizoctonia.*

The active component of the mycorrhiza may be the spores, hyphae, extramatrix arbuscular mycelium, glomalin and rootlets, colonized by the fungus in question.

Biocides

The liquid compositions of the present invention comprise a bactericide and/or a bacteriostat. A bactericide is an agent that kills bacteria and a bacteriostat is an agent, usually chemical, that prevents the growth of bacteria but that does not necessarily kill them or their spores.

Bactericides

The bactericide for use in the liquid compositions of the present invention may be a disinfectant, antiseptic or antibiotic.

A bactericidal disinfectant may be:

active chlorine (i.e., hypochlorites, chloramines, dichloroisocyanurate and trichloroisocyanurate, wet chlorine, chlorine dioxide, etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds, such as chlorhexidine, glucoprotamine, octenidine dihydrochloride, etc.), strong oxidizers, such as ozone and permanganate solutions;

heavy metals and their salts, such as colloidal silver, silver nitrate, mercury chloride, phenylmercury salts, copper sulfate, copper oxide-chloride, etc. Heavy metals and their salts are the most toxic, and environment-hazardous bactericides and therefore, their use is strongly oppressed or eliminated; further, also properly concentrated strong acids (phosphoric, nitric, sulfuric, amidosulfuric, toluenesulfonic acids) and alkalis (sodium, potassium, calcium hydroxides), such as of pH<1 or >13, particularly under elevated temperature (above 60° C.), kills bacteria.

A bactericidal antiseptic may be:

properly diluted chlorine preparations (e.g., Daquin's solution, 0.5% sodium or potassium hypochlorite solution, pH-adjusted, to pH 7-8, or 0.5-1% solution of sodium benzenesulfochloramide (chloramine B)), some iodine preparations, such as iodopovidone in various galenics (ointment, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid, some phenolic compounds, such as hexachlorophene, triclosan and Dibromol, and cation-active compounds, such as 0.05-0.5% benzalkonium, 0.5-4% chlorhexidine, 0.1-2% octenidine solutions.

A bactericidal antibiotic may be penicillin, cephalosporins, and aminoglycosidic antibiotics.

Other bactericidal antibiotics include the fluoroquinolones, nitrofurans, vancomycin, monobactams, co-trimoxazole, and metronidazole.

Preferred bactericides are:

Halogen containing compounds such as:
  Bronopol—active 2-bromo-2-nitro-1,3-propanadiol
  Dowicil 75—active 1-(3-chloroallyl)-3,5,7-triaza-1-azoniaadamantane chloride
  DBNPA—active dibromonitrilopropionamide
OrganoSulfurs—includes Isothaizolones such as:
  Proxel (Nipacide)—active 1,2-benzisothiazolin-3-one
  Kathon—active 5-chloro-2-methyl-4-isosthiazolin-3-one, 2-methyl-4-isosthiazolin-3-one
Nitrogen containing compounds such as:
  Germall II (Diazolidinyl urea)
  Tris nitro (tris(hydroxymethyl)nitromethane)
Phenolics such as:
  Dowicide (sodium o-phenylphenate)
Inorganics such as:
  copper arsenates
  cuprous oxide
Organometallics such as:
  compounds of arsenic, copper, mercury
Quaternary Ammonium Compounds Bacteriostats A bacteriostat is a biological or chemical agent that causes bacteriostasis. It stops bacteria from reproducing, while not necessarily harming them otherwise. Upon removal of the bacteriostat, the bacteria usually start to grow again.

Bacteriostats for use in the liquid compositions of the present invention include sodium azide and thimerosol.

Other bactericides and bacteriostats which can be used in the liquid compositions of the present invention are Glycopon, Ottasept (a combination of Proxel and propylene glycol), and EDTA (ethylenediamine tetraacetic add, a chelating agent).

Other Components in the Liquid Compositions

The liquid compositions of the present invention may include one or more of the following components:

1. Fertilizer Ingredients:
   a. Diammonium Phosphate
   b. Potassium Nitrate
   c. Urea
   d. Potassium Phosphate
   e. Potassium Bicarbonate
   f. Lidoquest Fe13P
   g. Lidoquest Mn13P
   h. Lidoquest Zn13P
   i. Potassium Chloride (KCl)
   j. Disodium Dihydro Molybdate
   k. Cobalt Chloride Hexahydrate
   l. Nickel Chloride Hexahydrate
   m. Caustic Potash Liquid
   n. MKP
   o. P-paraben/Nipasol
   p. Potassium thiosulfate
   q. Sodium hydroxide
2. Non-Nutritional Plant Beneficial Substances or Biostimulants
   a. Seaweed Extracts (*Ascophyllum nodosum*)
   b. Humic Acids
   c. Ascorbic Acid
   d. Thiamine mononitrate
   e. Potassium Sorbate (50% K Sorb)
   f. Myo-Inositol
   g. Glycine
   h. Vitamin E (alpha tocopherol)

Methods of Colonizing a Plant with Mycorrhiza

The present invention also relates to methods of increasing the colonization with one or more mycorrhizas comprising applying a liquid composition of the present invention to a plant, grass, tree or shrub.

The liquid composition can be applied in water by means of irrigation and fertigation systems.

The invention is further defined in the following paragraphs:

Paragraph 1. A liquid composition, comprising
   (a) one or more mycorrhizas; and
   (b) a bactericide and/or a bacteriostat.

Paragraph 2. The liquid composition of paragraph 1, wherein the one or more mycorrhizas are ectomycorrhizas.

Paragraph 3. The liquid composition of paragraph 2, wherein the ectomycorrhizas are of the phylum Basidiomycota.

Paragraph 4. The liquid composition of paragraph 3, wherein the ectomycorrhizas are strains of *Laccaria bicolor, Laccaria laccata, Pisolithus tinctorius, Rhizopogon amylopogon, Rhizopogon fulvigleba, Rhizopogon luteolus, Rhizopogon villosuli, Scieroderma cepa*, or *Scleroderma citrinum*.

Paragraph 5. The liquid composition of paragraph 1, wherein the one or more mycorrhizas are endomycorrhizas.

Paragraph 6. The liquid composition of paragraph 5, wherein the endomycorrhiza is of the phylum Zygomycota and order Glomales.

Paragraph 7. The liquid composition of paragraph 6, wherein the endomycorrhiza is a strain of *Gigaspora margarita, Glomus aggregatum, Glomus brasilianum, Glomus clarum, Glomus deserticola, Glomus etunicatum, Glomus fasciculatum, Glomus intraradices, Glomus monosporum*, or *Glomus mosseae*.

Paragraph 8. The liquid composition of paragraph 1, wherein the one or more mycorrhizas are ericoid mycorrhizas.

Paragraph 9. The liquid composition of paragraph 8, wherein the ericoid mycorrhizas are of the phylum Ascomycota.

Paragraph 10. The liquid composition of paragraph 9, wherein the ericoid mycorrhizas are *Hymenoscyphous ericae* or *Oidiodendron* sp.

Paragraph 11. The liquid composition of paragraph 1, wherein the one or more mycorrhizas are arbutoid mycorrhizas.

Paragraph 12. The liquid composition of paragraph 11, wherein the arbutoid mycorrhizas are preferably of the phylum Basidiomycota.

Paragraph 13. The liquid composition of paragraph 1, wherein the one or more mycorrhizas are monotripoid mycorrhizas.

Paragraph 14. The liquid composition of paragraph 13, wherein the monotripoid mycorrhiza are of the phylum Basidiomycota.

Paragraph 15. The liquid composition of paragraph 1, wherein the one or more mycorrhizas are orchid mycorrhizas.

Paragraph 16. The liquid composition of paragraph 15, wherein the orchid mycorrhizas are of the genus *Rhizoctonia*.

Paragraph 17. The liquid composition of paragraph 1, wherein the one or more mycorrhizas are a mixture of ectomycorrhizas and endomycorrhizas.

Paragraph 18. The liquid composition of paragraph 1, which comprises a bactericide.

Paragraph 19. The liquid composition of paragraph 18, wherein the bactericide is a disinfectant, antiseptic or antibiotic.

Paragraph 20. The liquid composition of paragraph 19, wherein the disinfectant is selected from the group consisting of
   a. active chlorine,
   b. active oxygen,
   c. iodine,
   d. concentrated alcohols,
   e. phenolic substances,
   f. cationic surfactants,
   g. strong oxidizers,
   h. heavy metals and their salts,
   i. properly concentrated strong acids, and
   j. alkalis.

Paragraph 21. The liquid composition of paragraph 19, wherein the antiseptic is selected from the group consisting of
   a. properly diluted chlorine preparations,
   b. iodine preparations,
   c. peroxides,
   d. alcohols with or without antiseptic additives,
   e. weak organic acids,
   f. phenolic compounds, and
   g. cation-active compounds.

Paragraph 22. The liquid composition of paragraph 19, wherein the antibiotic is selected from the group consisting of
   a. penicillin,
   b. cephalosporins,
   c. aminoglycosidic antibiotics,
   d. fluoroquinolones,
   e. nitrofurans,
   f. vancomycin, g. monobactams,
h. co-trimoxazole, and
i. metronidazole.

Paragraph 23. The liquid composition of paragraph 18, wherein the bactericide is selected from the group consisting of
a. 2-bromo-2-nitro-1,3-propanadiol,
b. 1-(3-chloroallyl)-3,5,7-triaza-1-azoniaadamantane chloride,
c. dibromonitrilopropionamide,
d. 1,2-benzisothiazolin-3-one,
e. 5-chloro-2-methyl-4-isosthiazolin-3-one, 2-methyl-4-isosthiazolin-3-one,
f. diazolidinyl urea,
g. tris(hydroxymethyl)nitromethane,
h. sodium o-phenylphenate,
i. copper arsenates,
j. cuprous oxide,
k. compounds of arsenic, copper, mercury, and
l. quarternary ammonium compounds.

Paragraph 24. The liquid composition of paragraph 1, which comprises a bacteriostat.

Paragraph 25. The liquid composition of paragraph 24, wherein the bacteriostat is sodium azide or thimerosol.

Paragraph 26. The liquid composition of paragraph 1, wherein the bactericide and/or the bacteriostat is Glycopon, Ottasept or EDTA.

Paragraph 27. The liquid composition of paragraph 1, which comprises a bactericide and a bacteriostat.

Paragraph 28. The liquid composition of paragraph 1, wherein the one or more mycorrhizas are present in an amount of 0.2-5%, preferably 0.33-3.3%.

Paragraph 29. The liquid composition of paragraph 1, wherein the bactericide and/or the bacteriostat is present in an amount of 50-3,000 ppm, preferably 150-2,000 ppm of the active ingredient.

Paragraph 30. The liquid composition of paragraph 1, which further comprises a fertilizer ingredient, preferably selected from the group consisting of
a. Diammonium Phosphate,
b. Potassium Nitrate,
c. Urea,
d. Potassium Phosphate,
e. Potassium Bicarbonate,
f. Lidoquest Fe13P,
g. Lidoquest Mn13P,
h. Lidoquest Zn13P,
i. Potassium Chloride (KCl),
j. Disodium Dihydro Molybdate,
k. Cobalt Chloride Hexahydrate,
l. Nickel Chloride Hexahydrate,
m. Caustic Potash Liquid,
n. MKP,
o. P-paraben/Nipasol,
p. Potassium thiosulfate, and
q. Sodium hydroxide.

Paragraph 31. The liquid composition of paragraph 1, which further comprises a non-nutritional plant beneficial substance or biostimulant, preferably selected from the group consisting of
a. Seaweed Extracts (*Ascophyllum nodosum*)
b. Humic Acids,
c. Ascorbic Acid,
d. Thiamine mononitrate,
e. Potassium Sorbate (50% K Sorb),
f. Myo-Inositol,
g. Glycine, and
h. Vitamin E (alpha tocopherol).

Paragraph 32. A method of increasing the colonization with one or more mycorrhizas, comprising applying a liquid composition of any of paragraphs 1-31 to a plant, grass, tree or shrub.

EXAMPLES

An endomycorrhizal mean infection percentage (MIP) bioassay was initiated to test mycorrhizal infectivity of a liquid mycorrhizal formulation treated with bactericides. The MIP bioassay is used to determine the effect of endomycorrhizal colonization in the roots of corn plants on the treatment applied. The MIP bioassay was adapted to utilize 15 mL of liquid per pot.

The liquid mycorrhizal formulation which was tested was MycoApply Ultra (Novozymes Biologicals), which is a mycorrhizal inoculant that contains several species of endomycorrhizas. For a ready to use fertilizer, the optimal amount of mycorrhizas to be added based on application rate of ready to use fertilizer, mycorrhizal infectivity, and cost effectiveness was 0.1 propagules of mycorrhizas per 1.0 mL of ready to use fertilizer. MycoApply Ultra contains 286 propagules per gram, therefore 0.00034 g MycoApply Ultra in 1 mL of ready to use fertilizer will provide the desired concentration of mycorrhizal propagules, 0.1 prop/mL.

The MycoApply Ultra was tested with two different concentrates 10× (0.0034 g/mL) and 100× (0.034 g/mL). The bactericide used in all treatments for Trial 1 was 500 ppm Kathon and 250 ppm Bronopol. There were seven treatment groups, each contained 5 replicates. Treatment 1 was a water only control. Treatment 2 was 10× concentrate MycoApply Ultra treated with bactericide made 10 days before treatment. Treatment 3 was 10× concentrate MycoApply Ultra treated with bactericide made 24 hours before treatment. Treatment 4 was 10× concentrate MycoApply Ultra untreated and made directly before treatment. Treatment 5 was 100× concentrate MycoApply Ultra treated with bactericide made 10 days before treatment. Treatment 6 was 100× concentrate MycoApply Ultra treated with bactericide made 24 hours before treatment. Treatment 7 was 100× concentrate MycoApply Ultra untreated and made directly before treatment. Each treatment was mixed in 100 mL of tap water.

Pots were filled within 2 cm of the top with a mix media 90:10 v/v blend of sand to peat. Two corn seeds (*Zea Maize* 'Golden Bantam') were planted in each pot and treatment groups were randomly assigned. On the day of planting 15 mL of each corresponding treatment was applied to each pot. Three additional 15 mL treatments were applied weekly following the initial treatment. The pots were placed in a growth chamber receiving 10 hours of light per day (Table 1) and were watered as needed. Upon germination of the seeds the plants were thinned to one seed per pot. The corn was harvested after 4 weeks of growth.

TABLE 1

10 hour growth chamber cycle used to grow corn.

| | | |
|---|---|---|
| a. | 6:00, 20° C., 55% RH, 2 Fluorescent, 2 Incandescent |
| b. | 7:00, 22° C., 55% RH, 4 Fluorescent, 2 Incandescent |
| c. | 10:00, 26° C., 65% RH, 6 Fluorescent, 8 Incandescent |
| d. | 15:00, 24° C., 65% RH, 4 Fluorescent, 4 Incandescent |
| e. | 18:00, 20° C., 55% RH, 0 Fluorescent, 0 Incandescent |

At harvest the parameter evaluated was percent mycorrhizal colonization.

Trial 2 was set up exactly like Trial 1, but with the addition of 2 more treatment groups. MycoApply Ultra was again tested with two different concentrates 10× (0.0034 g/mL) and 100× (0.034 g/mL). Trial 2 used the bactericides 500 ppm Kathon and 250 ppm Bronopol, but also added a 500 ppm Kathon alone treatment. There were nine treatment groups, each contained 5 replicates. Treatment 1 was a water only control. Treatment 2 was 10× concentrate MycoApply Ultra treated with 500 ppm Kathon and 250 ppm Bronopol made 10 days before treatment. Treatment 3 was 10× concentrate MycoApply Ultra treated with 500 ppm Kathon alone made 10 days before treatment. Treatment 4 was 10× concentrate MycoApply Ultra treated with 500 ppm Kathon and 250 ppm Bronopol made 24 hours before treatment. Treatment 5 was 10× concentrate MycoApply Ultra untreated and made directly before treatment. Treatment 6 was 100× concentrate MycoApply Ultra treated with 500 ppm Kathon and 250 ppm Bronopol made 10 days before treatment. Treatment 7 was 100× concentrate MycoApply Ultra treated with 500 ppm Kathon alone made 10 days before treatment. Treatment 8 was 100× concentrate MycoApply Ultra treated with 500 ppm Kathon and 250 ppm Bronopol made 24 hours before treatment. Treatment 9 was 100× concentrate MycoApply Ultra untreated and made directly before treatment. Each treatment was mixed in 100 mL of tap water. The rest of the methods follow Trial 1 exactly.

Results:

In both trials over the course of the studies plants in the 10× concentrate treatment received 0.204 g of MycoApply Ultra or 58.34 mycorrhizal propagules and plants in the 100× concentrate treatment received 2.04 g of MycoApply Ultra or 583.44 mycorrhizal propagules.

Percent mycorrhizal colonization produced significant differences ($\alpha=0.05$) between treatment groups and the control (Table 2). Plants grown in the 100× concentrates treated with bactericide, both 7 days old and 24 hours old, had a significantly higher percent mycorrhizal colonization than plants grown in the 100× concentrate untreated, the 10× concentrate untreated, and the control (Table 2). Plants grown in the 7 days old 100× concentrate treated with bactericide had a significantly higher percent mycorrhizal colonization compared to plants grown in the 10× concentrates treated with bactericides (Table 2). Plants grown in the 10× concentrates, both 7 days old and 24 hours old, had significantly higher percent mycorrhizal colonization compared to control plants (Table 2).

For Trial 2 percent mycorrhizal colonization was not statistically different ($\alpha=0.05$) between treatment groups and the control (Table 3). The plants grown in the 100× concentrate treated with 500 ppm Kathon and 250 ppm Bronopol 24 hours old had the highest percent colonization and was statistically different from all treatment groups except the 100× concentrate with the same bactericides at 7 days old (Table 3). All 100× concentrate treatment groups that contained bactericide treated MU had statistically higher percent colonization than the untreated 100× concentrate (Table 3). All 10× concentrate treatment groups that contained bactericide treated MU had statistically higher percent colonization than the untreated 10× concentrate (Table 3). All treatment groups that contained bactericide treated MU had a statistically higher percent colonization than the control (Table 3).

TABLE 2

Biocide Effect on Mycorrhizal Colonization Study I

| Treatment | Mean % Colonization | Standard Deviation | |
|---|---|---|---|
| Control | 3.00 | +/−3.71 | c |
| 10X MycoApply Ultra with 500 ppm Kathon & 250 ppm Bronopol made 7 days before treatment | 23.93 | +/−9.12 | b |
| 10X MycoApply Ultra with 500 ppm Kathon & 250 ppm Bronopol made 1 day before treatment | 18.40 | +/−15.81 | b |
| 10X MycoApply Ultra with no biocides | 9.93 | +/−3.61 | c |
| 100X MycoApply Ultra with 500 ppm Kathon & 250 ppm Bronopol made 7 days before treatment | 40.47 | +/−8.17 | a |
| 100X MycoApply Ultra with 500 ppm Kathon & 250 ppm Bronopol made 1 day before treatment | 34.33 | +/−6.51 | a |
| 100X MycoApply Ultra with no biocides | 7.27 | +/−3.76 | c |

TABLE 3

Biocide Effect on Mycorrhizal Colonization Study II

| Treatment | Mean % Colonization | Standard Deviation | |
|---|---|---|---|
| Control | 5.07 | +/−2.97 | de |
| 10X MycoApply Ultra with 500 ppm Kathon & 250 ppm Bronopol made 7 days before treatment | 19.93 | +/−1.23 | c |
| 10X MycoApply Ultra with 500 ppm Kathon & 250 ppm Bronopol made 1 day before treatment | 17.73 | +/−5.02 | c |
| 10X MycoApply Ultra with 500 ppm Kathon only made 1 day before treatment | 21.00 | +/−4.64 | ac |
| 10X MycoApply Ultra with no biocides | 9.40 | +/−2.77 | de |
| 100X MycoApply Ultra with 500 ppm Kathon & 250 ppm Bronopol made 7 days before treatment | 28.40 | +/−1.87 | ac |
| 100X MycoApply Ultra with 500 ppm Kathon & 250 ppm Bronopol made 1 day before treatment | 18.42 | +/−4.87 | c |
| 100X MycoApply Ultra with 500 ppm Kathon only made 1 day before treatment | 34.53 | +/−3.07 | ab |
| 100X MycoApply Ultra with no biocides | 14.67 | +/−6.89 | cd |

CONCLUSION

In Trial 1 the treatment of MycoApply Ultra with 500 ppm Kathon and 250 ppm Bronopol had a positive affect on the mycorrhizal infectivity of MycoApply Ultra. The 100× MycoApply Ultra treated with bactericide had 5 times greater mycorrhizal infectivity than 100× MycoApply Ultra untreated. The 10× MycoApply Ultra treated with bactericide had 2 times more mycorrhizal infectivity compared to the 10× MycoApply Ultra untreated.

In Trial 2 the treatment of MycoApply Ultra with 500 ppm Kathon and 250 ppm Bronopol and 500 ppm Kathon had a positive effect on the mycorrhizal infectivity of MycoApply Ultra. Trial 2 was set up to duplicate the results obtained from Trial 1. The results of Trial 2 mimic the results obtained from Trial 1 and show that treatment with Kathon and Bronopol increase mycorrhizal infectivity.

The results from both trials indicate that the presence of bactericide, specifically Kathon and Bronopol, increase the ability of mycorrhizas to germinate and infect roots.

We claim:

1. A liquid composition, comprising
   (a) one or more mycorrhizas; and
   (b) an amount effective of a bactericide and/or a bacteriostat for increasing mycorrhizal colonization.

2. The liquid composition of claim 1, wherein the one or more mycorrhizas are ectomycorrhizas.

3. The liquid composition of claim 1, wherein the one or more mycorrhizas are endomycorrhizas.

4. The liquid composition of claim 1, wherein the one or more mycorrhizas are ericoid mycorrhizas.

5. The liquid composition of claim 1, wherein the one or more mycorrhizas are arbutoid mycorrhizas.

6. The liquid composition of claim 1, wherein the one or more mycorrhizas are monotripoid mycorrhizas.

7. The liquid composition of claim 1, wherein the one or more mycorrhizas are orchid mycorrhizas.

8. The liquid composition of claim 1, wherein the one or more mycorrhizas are a mixture of ectomycorrhizas and endomycorrhizas.

9. The liquid composition of claim 1, which comprises a bactericide.

10. The liquid composition of claim 9, wherein the bactericide is a disinfectant, antiseptic or antibiotic.

11. The liquid composition of claim 9, wherein the bactericide is selected from the group consisting of
    a. 2-bromo-2-nitro-1,3-propanadiol,
    b. 1-(3-chloroallyl)-3,5,7-triaza-1-azoniaadamantane chloride,
    c. dibromonitrilopropionamide,
    d. 1,2-benzisothiazolin-3-one,
    e. 5-chloro-2-methyl-4-isothiazolin-3-one, 2-methyl-4-isothiazolin-3-one,
    f. diazolidinyl urea,
    g. tris(hydroxymethyl)nitromethane,
    h. sodium o-phenylphenate,
    i. copper arsenates,
    j. cuprous oxide,
    k. compounds of arsenic, copper, mercury, and
    l. quarternary ammonium compounds.

12. The liquid composition of claim 1, which comprises a bacteriostat.

13. The liquid composition of claim 12, wherein the bacteriostat is sodium azide or thimerosol.

14. The liquid composition of claim 1, which comprises a bactericide and a bacteriostat.

15. The liquid composition of claim 1, wherein the one or more mycorrhizas are present in an amount of 0.2-5%.

16. The liquid composition of claim 1, wherein the bactericide and/or the bacteriostat is present in an amount of 50-3,000 ppm of the active ingredient.

17. A method of increasing the colonization with one or more mycorrhizas, comprising applying a liquid composition of claim 1 to a plant, grass, tree or shrub.

18. The liquid composition of claim 15, wherein the one or more mycorrhizas are present in an amount of 0.33-3.3%.

19. The liquid composition of claim 1, wherein the bactericide and/or the bacteriostat is present in an amount of 150-2,000 ppm of the active ingredient.

20. The liquid composition of claim 9, wherein the bactericide is 5-chloro-2-methyl-4-isothiazolin-3-one, 2-methyl-4-isothiazolin-3-one.

21. The liquid composition of claim 9, wherein the bactericide is 2-bromo-2-nitro-1,3-propanadiol.

* * * * *